United States Patent
Bleicher et al.

(10) Patent No.: US 9,404,989 B2
(45) Date of Patent: Aug. 2, 2016

(54) METHOD FOR CALIBRATING A MEASURING DEVICE FOR INSPECTING SURFACES ON THE BASIS OF BARKHAUSEN NOISES FOR A SPECIFIED COMPONENT GEOMETRY

(71) Applicant: ZF Friedrichshafen AG, Friedrichshafen (DE)

(72) Inventors: Oliver Bleicher, Vancouver (CA); Herman Yakaria, Langenargen (DE); Yiwen Xu, Friedrichshafen (DE)

(73) Assignee: ZF Friedrichshafen AG, Friedrichshafen (DE)

(*) Notice: Subject to any disclaimer, the term of this patent is extended or adjusted under 35 U.S.C. 154(b) by 55 days.

(21) Appl. No.: 14/385,799

(22) PCT Filed: Mar. 4, 2013

(86) PCT No.: PCT/EP2013/054229
§ 371 (c)(1),
(2) Date: Sep. 17, 2014

(87) PCT Pub. No.: WO2013/149775
PCT Pub. Date: Oct. 10, 2013

(65) Prior Publication Data
US 2015/0061647 A1 Mar. 5, 2015

(30) Foreign Application Priority Data
Apr. 5, 2012 (DE) .......................... 10 2012 205 676

(51) Int. Cl.
*G01R 35/00* (2006.01)
*G01N 27/72* (2006.01)
*G01N 27/80* (2006.01)

(52) U.S. Cl.
CPC .............. *G01R 35/00* (2013.01); *G01N 27/725* (2013.01); *G01N 27/80* (2013.01)

(58) Field of Classification Search
CPC ....... G01N 27/725; G01N 27/80; G01R 35/00
USPC .......................................................... 324/202
See application file for complete search history.

(56) References Cited

U.S. PATENT DOCUMENTS 3,783,370 A   1/1974   Birdwell et al.
4,881,030 A   11/1989  Stuecker et al.
(Continued)

FOREIGN PATENT DOCUMENTS

DE   43 33 830 A1    4/1995
DE   196 01 027 A1   7/1997
(Continued)

OTHER PUBLICATIONS

T. Garstka, "The Influence of Product Thickness of the Measurements by Barkhausen Noise Method", Journal of Achievements in Materials and Manufacturing Engineering, Mar. 2008, vol. 27, issue 1, International OCSCO World Press 4 pages.
(Continued)

*Primary Examiner* — Jay Patidar
(74) *Attorney, Agent, or Firm* — Michael J. Bujold; Davis & Bujold, PLLC (57) ABSTRACT

A method for enhancing inspection of components of specific geometry based on Barkhausen noises. The method includes specifying a first calibration curve that is independent of the component geometry, which describes the relationship between surface hardness values and measured Barkhausen noise signals. A first noise signal is determined by the measuring device for a reference component having the specified geometry and a first hardness value. A second noise signal is determined for a second reference component, having the specified geometry and a second hardness value lower than the first. A second calibration curve is determined, in which the first calibration curve is fitted to the first noise signal at the first hardness value and to the second noise signal at the second hardness value, such that using the second calibration curve, the measured noise signal of a component having the specified geometry relates with a surface hardness value.

17 Claims, 9 Drawing Sheets

(56) References Cited

U.S. PATENT DOCUMENTS 5,619,135 A 4/1997 Kohn et al.
5,992,241 A * 11/1999 Posgay ............... G01N 27/725
 324/209

FOREIGN PATENT DOCUMENTS

| | | |
|---|---|---|
| DE | 10 2007 001 464 A1 | 7/2008 |
| EP | 0 100 009 A1 | 2/1984 |
| EP | 0 125 064 A2 | 11/1984 |
| EP | 0 287 873 A2 | 10/1988 |
| WO | 96/10744 A1 | 4/1996 |
| WO | 2008/080395 A2 | 7/2008 |

OTHER PUBLICATIONS

Suvi Santa-Aho et al, "Development of Barkhausen Noise Calibration Blocks for Reliable Grinding Burn Detection", Journal of Materials Processing Technology, Oct. 4, 2011, vol. 212, No. 2, pp. 408-416, Elsevier, Netherlands 9 pages.
German Search Report Corresponding to 10 2012 205 676.9 mailed Jan. 2, 2013 6 pages.
German Search Report Corresponding to 10 2012 205 677.7 mailed Jan. 2, 2013 6 pages.
International Search Report Corresponding to PCT/EP2013/054229 mailed May 21, 2013 7 pages.
International Search Report Corresponding to PCT/EP2013/054230 mailed May 27, 2013 4 pages.
Written Opinion Corresponding to PCT/EP2013/054229 mailed May 21, 2013 9 pages.

* cited by examiner

METHOD FOR CALIBRATING A MEASURING DEVICE FOR INSPECTING SURFACES ON THE BASIS OF BARKHAUSEN NOISES FOR A SPECIFIED COMPONENT GEOMETRY

This application is a National Stage completion of PCT/EP2013/054229 filed Mar. 4, 2013, which claims priority from German patent application Ser. No. 10 2012 205 676.9 filed Apr. 5, 2012.

FIELD OF THE INVENTION

The invention concerns a method for the calibration of a measuring device for surface inspection on the basis of Barkhausen noises for a specific component geometry, and a corresponding measuring device.

BACKGROUND OF THE INVENTION

In the industrial production of components, during surface machining damage may occur. Particularly in the mass production of components it is therefore necessary by means of a suitable inspection method to recognize such damage so that the damaged components can be separated out and the production process modified so as to avoid it.

A frequently occurring form of surface damage is the so-termed grinding burn, which for example can take place during tooth grinding to produce the final contour of toothed components. For the recognition of surface damage or grinding burn, from the prior art, chemical etching methods are known. During so-termed Nital etching the component to be inspected is treated with various acids and electrolytes such that after the treatment surface damage and particularly grinding burn can be recognized by virtue of color changes on the component. Nital etching is on the one hand not environmentally friendly, and on the other hand it incurs very high costs for the maintenance and disposal of the acids and electrolytes used. Furthermore, it is a subjective inspection method in which the surface damage is assessed by human experts by virtue of the discoloration. Thus, Nital etching is not suitable for inspecting the surface of components in the context of mass production.

From the prior art, the so-termed Barkhausen Noise Analysis is also known, with which the surface of ferromagnetic materials can be inspected by means of appropriate sensors. In the documents EP 0 100 009 A1 and DE 43 33 830 A1, methods for surface analysis taking account of Barkhausen noises are described. Barkhausen Noise Analysis is based on the so-termed Barkhausen jumps, which are produced by the reversal of magnetization in ferromagnetic materials in a magnetic field of slowly increasing strength. Ferromagnetic materials consist of small magnetic regions (called domains) with a uniform magnetization direction. The domains are separated from one another by Bloch walls, within which the magnetization direction changes through the width of the walls. A movement of the Bloch walls can be brought about by an external magnetic field. If at the same time a coil is positioned close to the ferromagnetic component, the magnetization produces an electric pulse in the coil. Addition of the impulses produces a noise-like signal, also known as Barkhausen noise or a Barkhausen noise signal. The Barkhausen noise signal depends on the surface condition and in particular on the surface hardness. By means of the Barkhausen noise signal grinding burn can be detected, since grinding burn reduces the surface hardness.

Since the Barkhausen noise depends not only on the surface condition of the component but also on other influencing parameters and particularly on the component geometry, a suitable calibration of a measuring device for Barkhausen noise analysis is necessary for the specific component geometry concerned. Here and in what follows 'component geometry' is understood to mean the specification of the dimensions of the component, as defined for example on a design drawing. Conventionally, calibration for a specific component geometry is a very elaborate process since for this several components with that geometry have to be used, which have to be made deliberately with different degrees of surface damage, for example different grinding burn severities. For this the components can for example be produced by grinding them with graded feed rates. The components so prepared are then inspected using the measuring device to be calibrated, i.e. the corresponding Barkhausen noise signals are recorded by the measuring device. Then, the components are graded in terms of their surface damage by Nital etching so that the surface damage can be correlated with the Barkhausen noise signals. As mentioned, this calibration process has to be carried out for each component geometry. Moreover, the calibration must be repeated whenever the sensor element of the measuring device is replaced. Furthermore, the controlled production of surface damage or grinding burn is very difficult in practice. Thus, Barkhausen noise analysis is not well suited for serial measurements of components having numerous variants.

SUMMARY OF THE INVENTION

The purpose of the present invention is therefore to provide a method for the simple and quick calibration of a measuring device for surface inspection, based on Barkhausen noise for a specific component geometry.

This objective is achieved by the method and the measuring device described below.

In the method according to the invention, a first calibration curve that is independent of the component geometry is specified, which describes the dependence between surface hardness values and the measured Barkhausen noise signals. This curve is independent of the component geometry in the sense that it is valid for any (arbitrary) component geometry. However, the curve is preferably determined for a particular material, so the calibration is also only valid for components made from the said material. In this case the first and second reference components, which will be described later, must also consist of the same specific material. The first calibration curve is preferably determined in such manner that it is stored in an appropriate memory in the measuring device.

The first calibration curve describes the approximate relation between surface hardness values and Barkhausen noise signals. It portrays the trend of how the Barkhausen noise signals vary in line with the surface hardness variation of arbitrary components. Thus, the first curve need only be determined once and can then be used for any component geometry. The determination of the first calibration curve is described in more detail later on.

Besides the first calibration curve, for the purposes of the calibration process a first reference component and a second reference component are used. For the first reference component, whose geometry corresponds to the specific component geometry concerned and which has a first surface hardness value, a first Barkhausen noise signal is determined by the measuring device to be calibrated. Then, for a second reference component, whose geometry also corresponds to the specific component geometry concerned but which has a second surface hardness value lower than the first surface hardness value, a second Barkhausen noise signal is determined by the measuring device being calibrated. Otherwise than in the prior art, here it is only necessary to ensure that by means of a suitable production process a first and a second reference component can be made, whose surface hardness values differ, without having to use elaborate methods to produce various degrees of surface damage in the components.

To determine a second calibration curve specifically for the component geometry concerned, in the method according to the invention the first calibration curve is fitted to the first Barkhausen noise signal at the first surface hardness value and to the second Barkhausen noise signal at the second surface hardness value and, for this, well-known curve adaptation methods can be used. Thus, by way of the second calibration curve, during the operation of the measuring device the measured Barkhausen noise signal of the component can be associated with a surface hardness value.

The calibration method according to the invention needs only two reference components, whose Barkhausen noise signals are detected during the calibration process. Taking into account the first calibration curve, the one that is independent of component geometry, it is then possible to determine a geometry-dependent, second calibration curve in a suitable manner. By means of that curve surface hardness values, which are as a rule correlated with specific surface damage types, can be determined from the Barkhausen noise signals.

In a preferred embodiment the first calibration curve is fitted in such manner that the value of the second calibration curve corresponds to the first Barkhausen noise signal at the first surface hardness value and the value of the second calibration curve corresponds to the second Barkhausen noise signal at a second surface hardness value. If necessary other curve fits as well can be used, with which the second calibration curve does not pass exactly through the first or second Barkhausen noise signal.

In a particularly preferred embodiment of the calibration according to the invention, respective limit values of the Barkhausen noise signal are associated by means of the second calibration curve with one or more specified surface hardness values. In this way, in particular various component damage types can be represented by limit values of the Barkhausen noise, so that if the said limit values are exceeded or fallen below, the corresponding surface damage is detected by the measuring device. In a preferred embodiment the specific component damage types for which limit values of the Barkhausen noise signal are established, are grinding burn stages of a component produced by grinding. In a preferred variant the component to be inspected is a gearwheel.

In a further preferred embodiment the first calibration curve used in the calibration process is an experimentally determined calibration curve. In this case the experimental determination is preferably designed such that for a number of components, various degrees of experimentally produced surface damage are correlated with surface hardness values by measuring the surface hardness, and those various degrees of experimentally determined surface damage are in turn correlated with Barkhausen noise signals by the measurement of Barkhausen noises. Since the two correlations are linked by the degrees of surface damage, a relationship can be determined thereby between surface hardness values and Barkhausen noise signals and in this way the first calibration curve can be determined. The components used for determining the first calibration curve can have different geometries and in particular do not have to correspond with the specific component geometry for which the measuring device is being calibrated. In a preferred embodiment the surface damage is determined experimentally by Nital etching as already described earlier. In this case, however, the Nital etching only has to be carried out once for a given material and not for every component geometry.

In a further preferred embodiment, for the first reference component and for the second reference component a respective particular production process for producing each of the components is specified. When the production process for the components is carried out, this ensures that two components with different surface hardness values are produced. In particular, the production process is designed such that the reference components have uniform surface hardness, so that when the reference components are measured using the measuring device to be calibrated, a substantially constant Barkhausen noise signal is obtained.

In a particularly preferred embodiment, the production process for the second reference component differs from the production process for the first reference component exclusively in that the production process for the second reference component has an additional component heat treatment step. By appropriate specification of that heat treatment the surface hardness can be made lower by comparison with the first reference component.

In another version of the method according to the invention, an upper and a lower limit value for the surface hardness of the component with the specific component geometry are defined, and by means of the second calibration curve upper and lower Barkhausen noise signal values are associated with those limit values. In this case the upper and lower surface hardness limit values determine a tolerance range, which in particular is specified on the design drawing of the component having the specific geometry. This is intended to ensure that the said tolerance range is not departed from. That can be achieved by suitably establishing an upper and a lower limit for the Barkhausen noise signal using the second calibration curves. If the corresponding limit values are exceeded or fallen below, this can then be detected by the calibrated measuring device.

In a further, particularly preferred variant of the method according to the invention, during the inspection of a component the calibration is again adapted in a component-internal manner. For this, with a component with the specific geometry that has just been inspected using the measuring device a surface region without any surface damage is determined, and in the event that the minimum Barkhausen noise signal in the said surface region having no surface damage is higher than the Barkhausen noise signal from the first reference component, the lower limit is increased by the difference between these two Barkhausen noise signals and the upper limit value is changed as a function of that difference. This variant of the invention makes use of the recognition that as a rule every component will comprise an area where there is no surface damage. Consequently, the limit values can be adapted still more accurately, specifically for the component concerned. In the more detailed description it will be explained how a surface area with no surface damage can be appropriately identified from the corresponding Barkhausen noise signals.

In a further embodiment of the invention, a self-calibration of the device takes place by virtue of the cumulative number of components measured in a series. In this case, during the series measurement of a large number of identical components an overall Barkhausen noise signal is determined, which can be for example the average value of all the Barkhausen noise signals measured along the surface of the component. By means of a statistical evaluation of overall signals from a number of identical components during a run-up phase before the series measurement, a significance level is determined with which, during the series measurement, for each overall signal a tolerance range for the overall signal is determined, and any departure from that tolerance range is detected.

In a particularly preferred embodiment, in the course of the statistical evaluation an outrider recognition process of the overall signals is carried out by methods known per se, and the significance level is adapted depending on whether the outrider is a component with or without surface damage. Thus, by virtue of this method it is known for the corresponding components whether or not they have surface damage. The surface damage can be detected by methods known per se, for example hardness measurements or internal stress measurements. In particular, the significance level is adapted in such manner that if an outrider corresponds to a component with no surface damage, the significance level is lowered, whereby the tolerance range is increased. In contrast, if the component according to the outlier has surface damage, the significance level is not changed. In a further preferred variant the tolerance range is also adapted if necessary during the series measurement. In that case, during the series measurement it is determined on a random basis for overall signals outside the tolerance range whether the corresponding component associated with the overall signal has any surface damage, and the tolerance range is increased if the component has no surface damage.

Besides the method described, the invention also concerns a measuring device for surface inspection based on Barkhausen noises for a specific component geometry. In this, in a memory of the measuring device a first calibration curve independent of the component geometry is stored, which describes the dependence between surface hardness values and measured Barkhausen noise signals. Furthermore, for a first reference component with the specified geometry and with a first surface hardness value, a first Barkhausen noise signal can be determined by the measuring device during its calibration. Likewise, for a second reference component with the specified geometry and with a second surface hardness value lower than the first surface hardness value, a second Barkhausen noise signal can be determined by the measuring device during its calibration.

The measuring device according to the invention comprises a computer unit by means of which a second calibration curve is determined during the calibration of the measuring device, in that the first calibration curve is fitted to the first Barkhausen noise signal at the first surface hardness value and to the second Barkhausen noise signal at the second surface hardness value, in such manner that by means of the second calibration curve, during the operation of the measuring device the measured Barkhausen noise signal from a component having the specific component geometry can be associated with a surface hardness value.

The measuring device according to the invention is preferably designed such that one or more of the preferred variants of the calibration process according to the invention can be implemented by means of the device.

BRIEF DESCRIPTION OF THE DRAWINGS

Example embodiments of the invention will be described in detail below with reference to the attached figures, which show.

DETAILED DESCRIPTION OF THE PREFERRED EMBODIMENTS

Below, the method according to the invention based on a calibration of a measuring device for the surface inspection of components in the form of gearwheels is explained. Nonetheless, the invention can also be used for components of any other type. In the present case, during the manufacture of the gearwheels their final contour is produced by tooth-grinding. During this grinding process the excess material is worn away by grinding grains. This can cause the local temperatures at the contact zone to change so markedly that thermal structural changes take place. These thermal structural changes are often known as grinding burn. It is one objective of the embodiment of the invention described here, by means of an appropriately calibrated measuring device to recognize such components as having surface damaged by grinding burn. Grinding burn is produced, inter alia, if the component-specific annealing temperature is exceeded and occurs in the form of tempering damage as a result of which the hardness at the points affected in the component decreases. If the temperature is increased drastically followed by cooling due to the coolant medium, a harder surface is produced. That form of grinding burn is also referred to as re-hardening.

In the embodiment described here, damage in gearwheels is recognized by means of a measuring device on the basis of Barkhausen noises. As already explained earlier, Barkhausen noises are measured by applying an external magnetic field at corresponding points of the surface of a component being inspected. By means of a coil of conductive wire, the magnetization produced gives rise to an electrical pulse in the coil, which depends on the surface hardness. By addition of the electric pulses $x_i$ a noise-like signal is obtained. Then, as a rule, the effective value of the Barkhausen signal is used as a measurement value, which is given by the following equation:

$$mp = \sqrt{\frac{1}{n}\sum_{i=0}^{n-1} x_i^2}. \tag{1}$$

The abbreviation mp, known per se, in this case represents the magnetic parameter.

Figure 1:
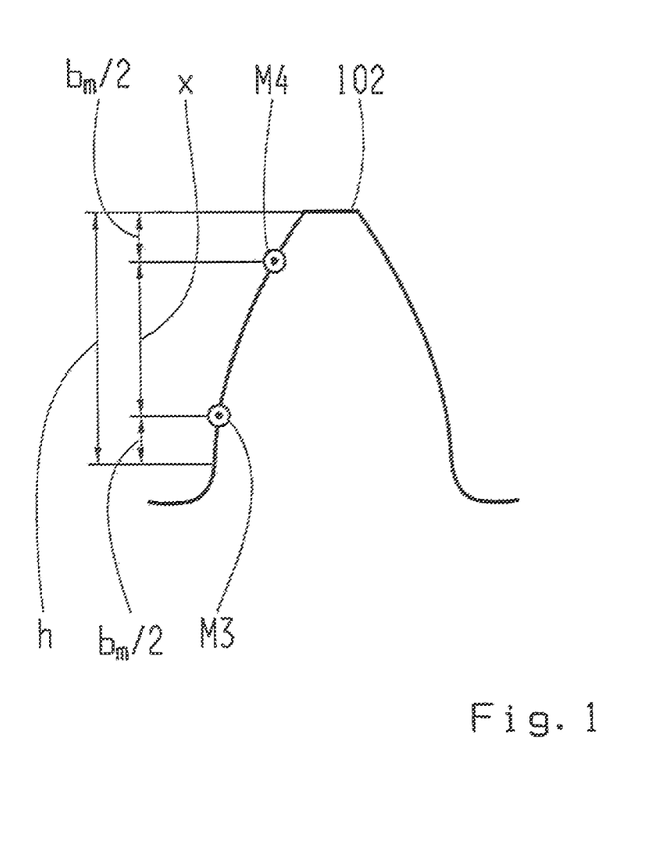
FIGS. 1 and 1A: A schematic representation of the measurement process based on Barkhausen noises, for a gearwheel.
Figure 1A:
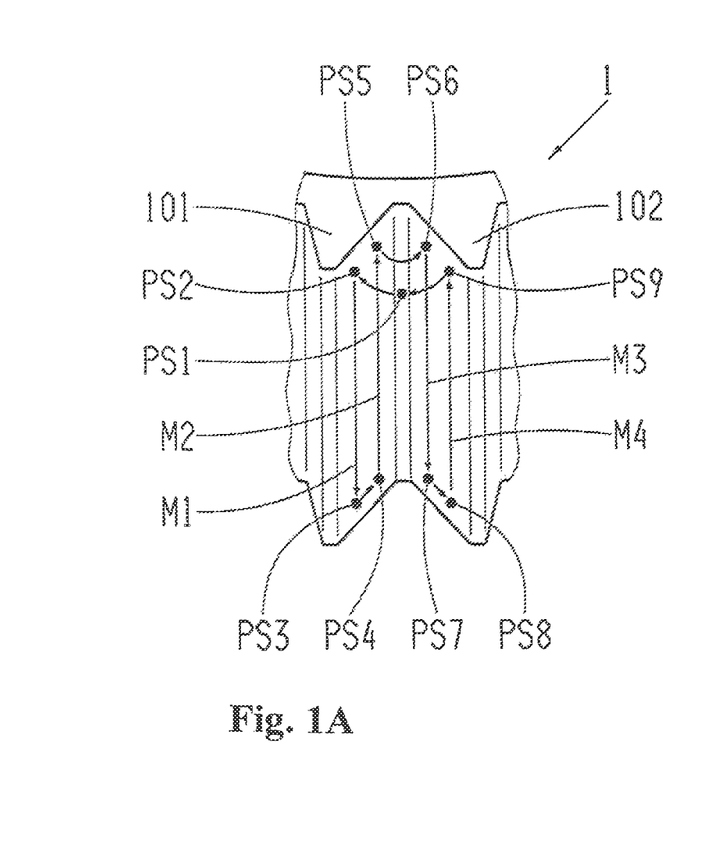

FIGS. 1 and 1A show a measurement sequence for determining the Barkhausen noise for a gearwheel. FIG. 1A shows in perspective a tooth gap of the gearwheel. This tooth gap is between the two teeth 101 and 102, which are only shown in part. To measure the Barkhausen noise signal an appropriate sensor head of the measuring device is moved along the measurement lines M1 to M4, during which process the Barkhausen noise signal is measured continuously. FIG. 1A shows as an example a measurement sequence in which the measuring head starts from the point PS1 and moves first to the surface point PS2 on tooth 101 and then along the measurement line M1 to point PS3. This is then followed by a further measurement from point PS4 as far as point PS5 along the measurement line M2. By analogy, for the tooth 102 measurements are made first along the measurement line M3 from point PS6 to point PS7, and finally along the measurement line M4 from point PS8 to point PS9. FIG. 1 shows a sectioned view of the tooth 102. One can see the measurement lines M3 and M4 perpendicular to the plane of the drawing. Here, the dimension h represents the tooth height that can be used for measuring, while the dimensions $b_m/2$ indicate the corresponding distances of the measurement lines M3 and M4 from the lower and upper ends of the useful tooth height. The distance between M3 and M4 is shown as x.

The signal intensity of the Barkhausen noise for well-prepared (i.e. dirt- and oil-free) components are influenced by the internal stresses and the hardness of the component. For example, a reduction of the compression condition results in an increase of the Barkhausen noise amplitude. When the hardness changes, the contrary is observed, i.e. as the hardness increases the Barkhausen noise amplitude decreases. In the embodiment of Barkhausen noise analysis described here this effect is used in order to detect the condition of the component with regard to its surface hardness by measurement technology and to relate it to grinding burn.

Since Barkhausen noise analysis measures the hardness or condition of components not directly but indirectly with reference to the Barkhausen noise, the measuring device used has to be suitably calibrated. In particular the Barkhausen noise signal, also called the BNA signal in what follows, also depends on the component geometry so the measuring device has to be calibrated for the component geometry to be measured. In the embodiment of the invention described here, during the calibration a limit value for the BNA signal or its amplitude is established, and this limit value is correlated with a condition of the component in which it exists shortly before the grinding burn is produced. If necessary corresponding limit values can also be established for various stages of grinding burn (i.e. various degrees of grinding burn) by means of the calibration process.

Otherwise than in the prior art, it is not necessary first to carry out an elaborate production process of corresponding components conforming to the actual geometry to be measured but having various degrees of grinding burn, which are then tested using the Barkhausen noise measuring device for calibration purposes. Rather, it is sufficient to produce only two reference components, also referred to as master components in what follows, using a specified and repeatable production process, and then use these for calibration.

In the context of the calibration method described here, one starts with a component-independent first calibration curve of the BNA signals for assessing surface damage or grinding burn, which is stored in advance in the corresponding measuring device. This first calibration curve is then fitted by means of the Barkhausen noise signals measured for the reference components using the measuring device, as explained in more detail later. The second calibration curve so produced can then be used to correlate corresponding surface hardness values or grinding burn degrees with limit values of the Barkhausen noise signals. During operation of the calibrated measuring device, if the corresponding limit values are exceeded or fallen below it is then possible to emit warnings or to classify the component as a reject. In special embodiments there is also the possibility that in the context of a statistical evaluation of the measurement values from a single component, the corresponding limit values of the Barkhausen noise signals can be adapted afresh for that component. Furthermore, the component-specific limit values can if necessary be re-adapted by virtue of statistical evaluation of the measurement values from a plurality of components measured in series.

Figure 2:
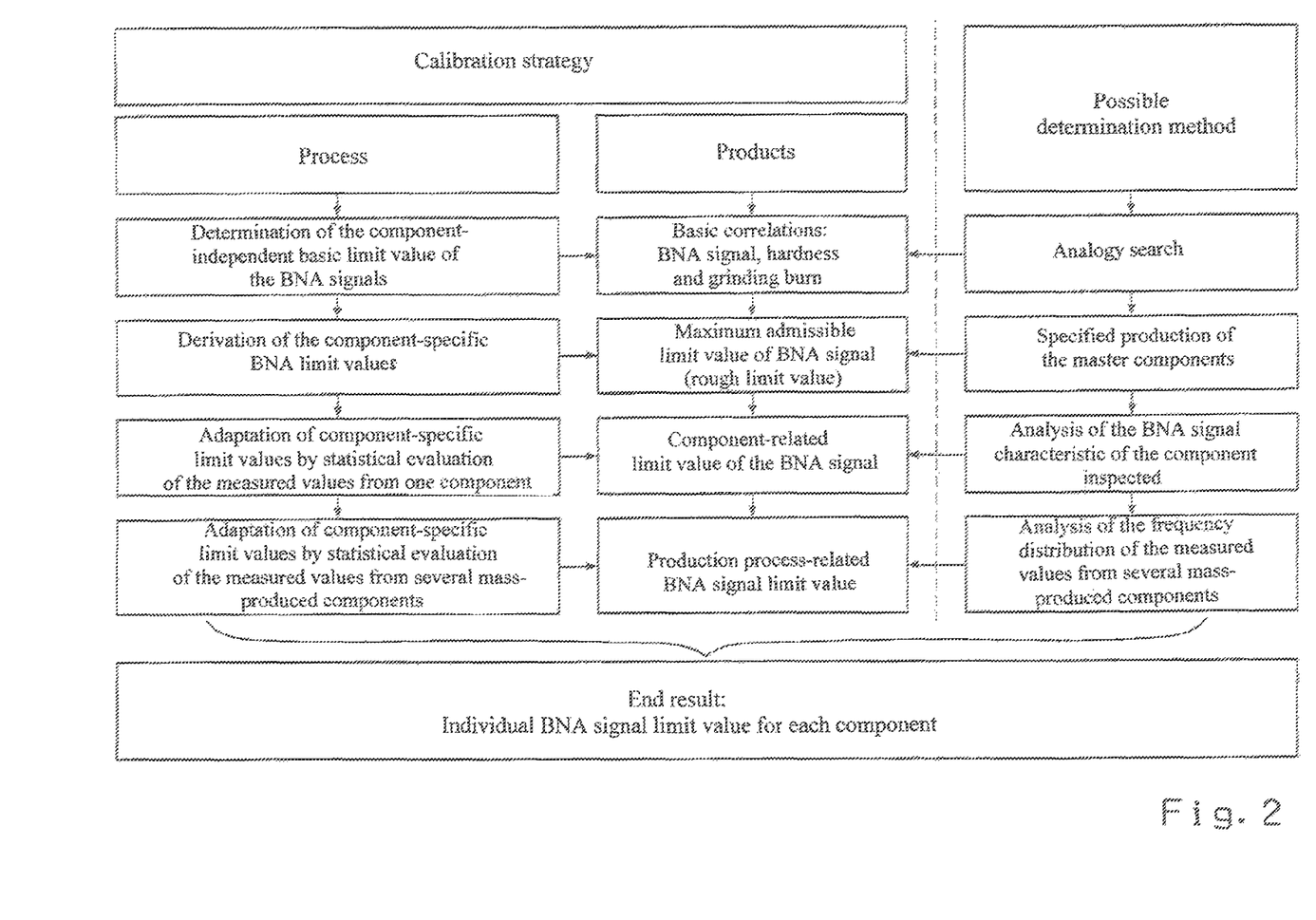
FIG. 2: A diagram to make clear the parameters used during a calibration according to the invention, and their determination.

FIG. 2 shows a diagram which makes clear the parameters required for the purposes of the calibration strategy according to the invention, and their determination. First, a component-independent first calibration curve and corresponding basic limit values of the BNA signal are determined, which make clear for any arbitrary components the basic correlation between the BNA signal and the hardness or grinding burn. The basic correlation is determined, for example, by searching for analogies. The correlations to be determined generally depend on the material used and can be determined by various experimental methods. For example, the method of surface grinding round carburized specimens or the tooth grinding of particular components, or else a grinding burn simulation by a laser technique can be used. In this way grinding burn of various intensities can be produced for corresponding components. The geometry of the components does not have to correspond with those measured later with the measuring device, since it is only necessary to recognize a trend of the Barkhausen noise signals as a function of the grinding burn. When the thermally damaged components have been prepared, they are then finally inspected for grinding burn by Nital etching. From this the degrees of grinding burn are deduced on the basis of the corresponding discolorations on the component surface produced by the Nital etching. In the next step the components are measured at defined points affected by grinding burn damage, by means of Barkhausen noise analysis. For this measurement, any measuring device can be used. In particular, the measuring device to be calibrated does not have to be used for this. In addition, at the defined points with grinding burn another method is used to make hardness measurements. In this way the measured BNA signals can be associated with the corresponding component surface hardness values at particular measurement points. Finally, a correlation is established between the BNA signals and the component surface hardness values by means of a regression equation, whereby a first calibration curve is obtained. Likewise, the correlation between grinding burn degrees and component surface hardness values can be described mathematically by a regression equation.

Figure 3:
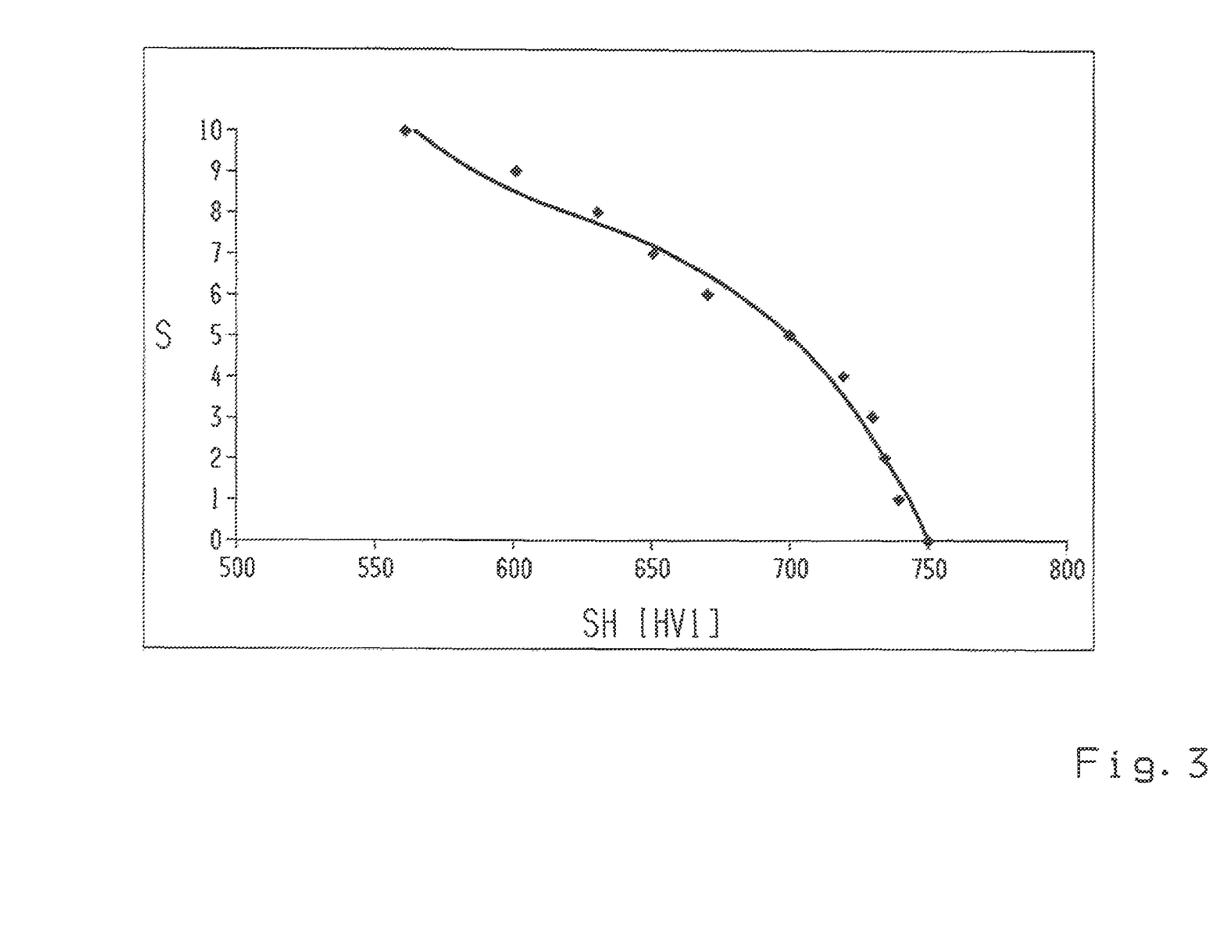
FIG. 3: A diagram which makes clear the experimentally determined relationship between the surface hardness and the grinding rim stage of a gearwheel.
Figure 4:
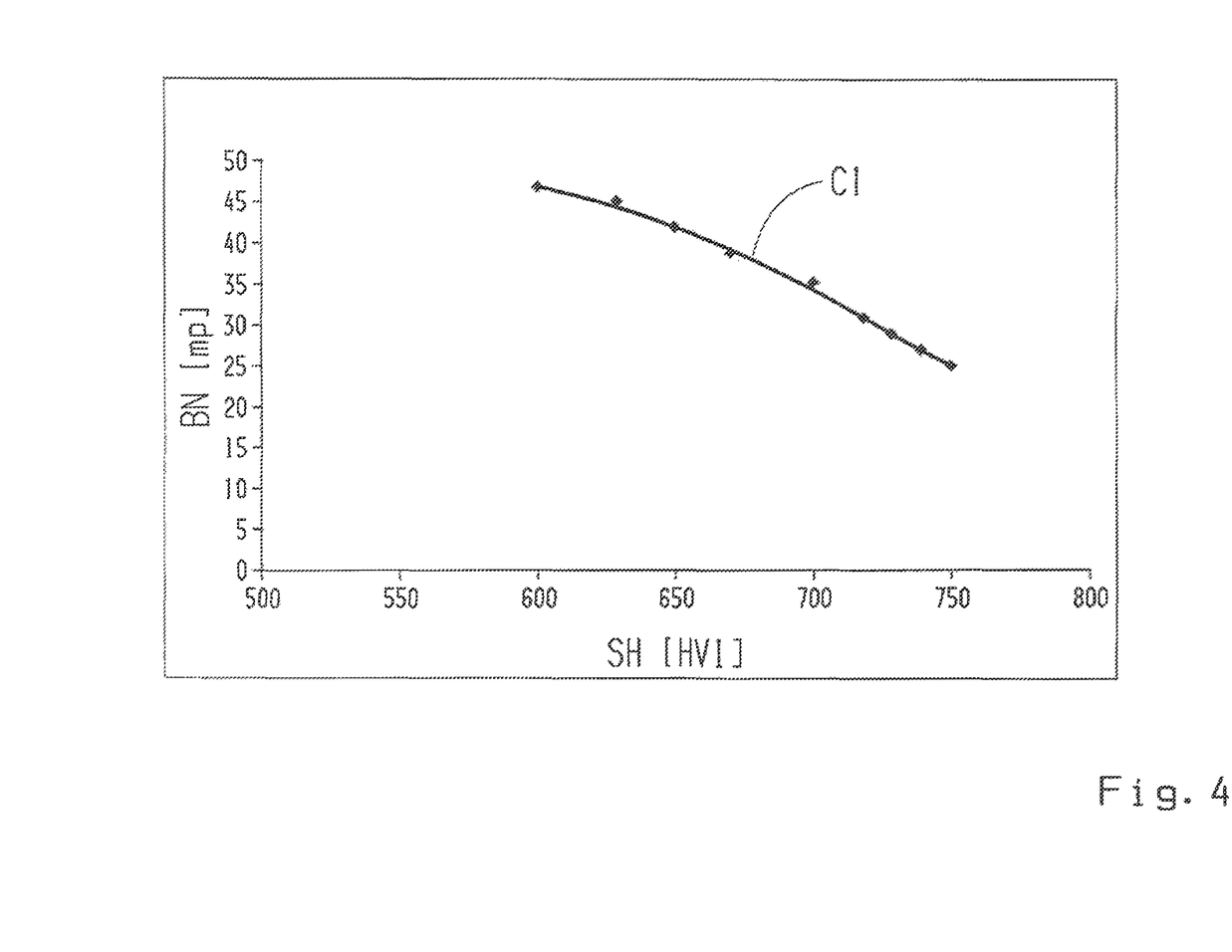
FIG. 4: A diagram illustrating an embodiment of the first calibration curve used in the context of the method according to the invention.

FIG. 3 shows a determined relationship between grinding hardness levels determined by Nital etching and surface hardness values determined by a separate method. The surface hardness SH (measured in HV1) is plotted along the abscissa and the grinding burn intensity S between values of 0 and 10 is shown along the ordinate. By corresponding measurements of the Barkhausen noise signals at the damaged surfaces of the component, a correlation of those signals with the surface hardness can be established and thereby the first calibration curve C1 is obtained, which is shown in FIG. 4. In that figure, for various surface hardness values SH, the associated Barkhausen noise signals BN are plotted, and the calibration curve C1 is determined by an appropriate polynomial fit. Thus, during the determination of the first calibration curve C1 correlations between the phenomenon itself (grinding burn detected by Nital etching), physical properties (surface hardness) and the measured parameter (BNA signals) are used as the basis for the calibration. Since grinding burn is recognized by the Nital testing by virtue of the etched color alteration compared with the undamaged area on the same component, while the discolorations depend in principle on the component surface hardness values, the component surface hardness is the dominant physical parameter by means of which grinding burn is identified.

As shown in FIG. 2, the first calibration curve is used for the derivation of component-specific BNA limit values. For this a rough, maximum admissible limit value for the BNA signal of a component with a specific component geometry is determined, and for that purpose specially prepared master components are used. These master components correspond to the components to be measured later by the calibrated measuring device. In other words, the master components have the same geometry or dimensions as the components to be inspected, and also consist of the same material.

With the help of the master components, the information obtained by determining the first calibration curve is adapted individually for each component. In this way the fact is taken into account that the BNA signals depend not only on the surface hardness, but also on the geometry of the component. The two master components are produced by selective heart processes. The first master component corresponds to the "good" condition, namely the grinding burn free condition is represented by this first master component. The second master component corresponds to the "bad" condition, i.e. the grinding burn damaged condition is represented by that master component. The master components are made in accordance with a specified production sequence, examples of which are shown in FIG. 5.

Figure 5:
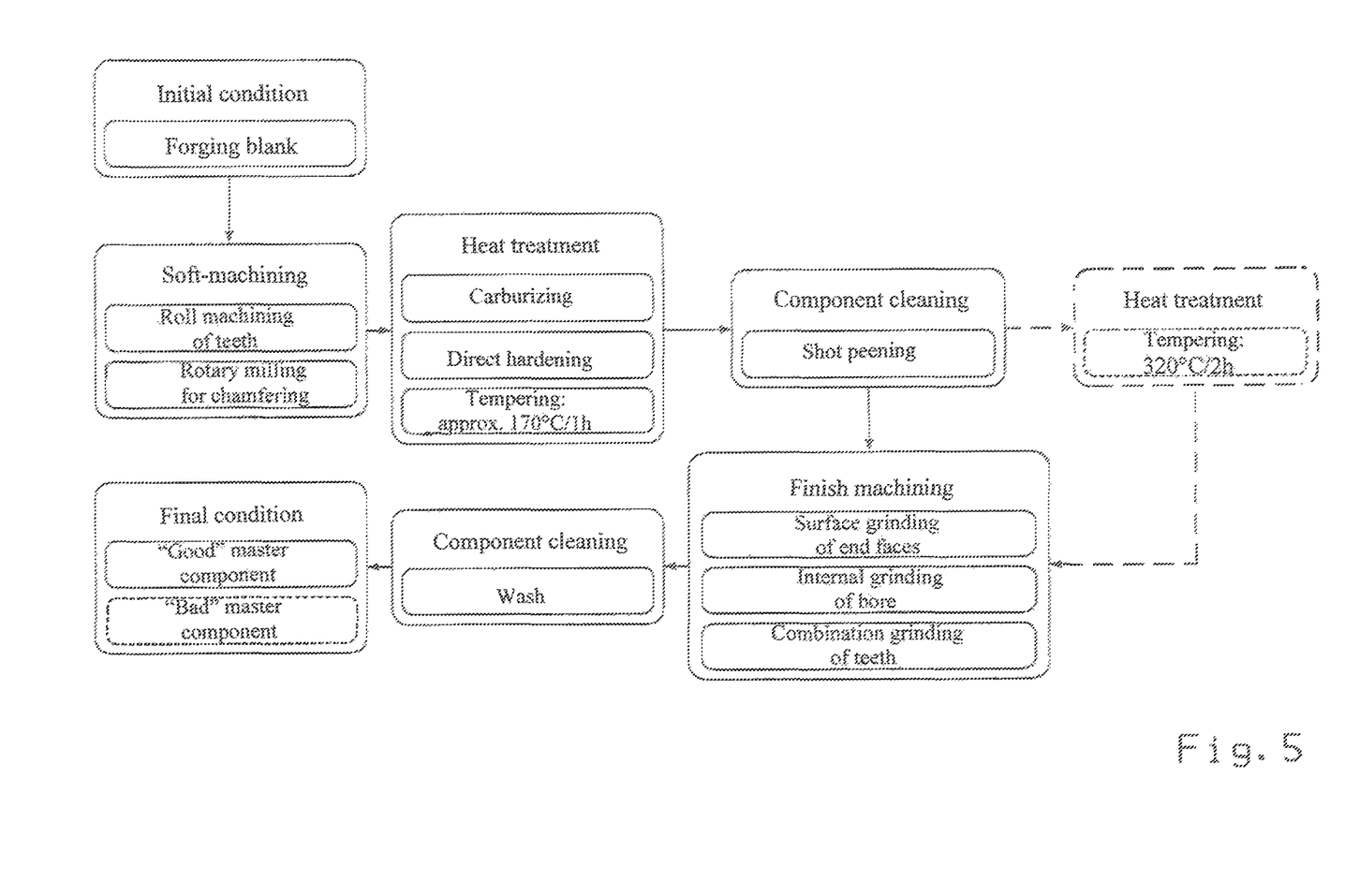
FIG. 5: A schematic representation illustrating the production of a first and a second reference component, based on an embodiment of the invention.

According to FIG. 5 a master component in its initial condition is at first a forging blank, which then undergoes a soft-machining process such as hobbing to produce teeth or rotary milling for chamfering. The component then undergoes a heat treatment such as carburizing, direct hardening and tempering at a temperature of around 170° C. for an hour. Finally the component is cleaned for the first time by ball peening. For the production of the first master component, which represents the "good" condition, immediately after the cleaning stage a hard finishing process takes place, such as the surface grinding of end faces, the internal cylindrical grinding of bores or the combination grinding of teeth. Finally the component is cleaned again. In its finished condition the first master component is in the "good" condition. The same steps are also carried out for the second master component in the "bad" condition, but in addition after the first cleaning of the component and before the hard finishing the component is heat treated by annealing at 320° C. for two hours, to simulate grinding burn.

Figure 6:
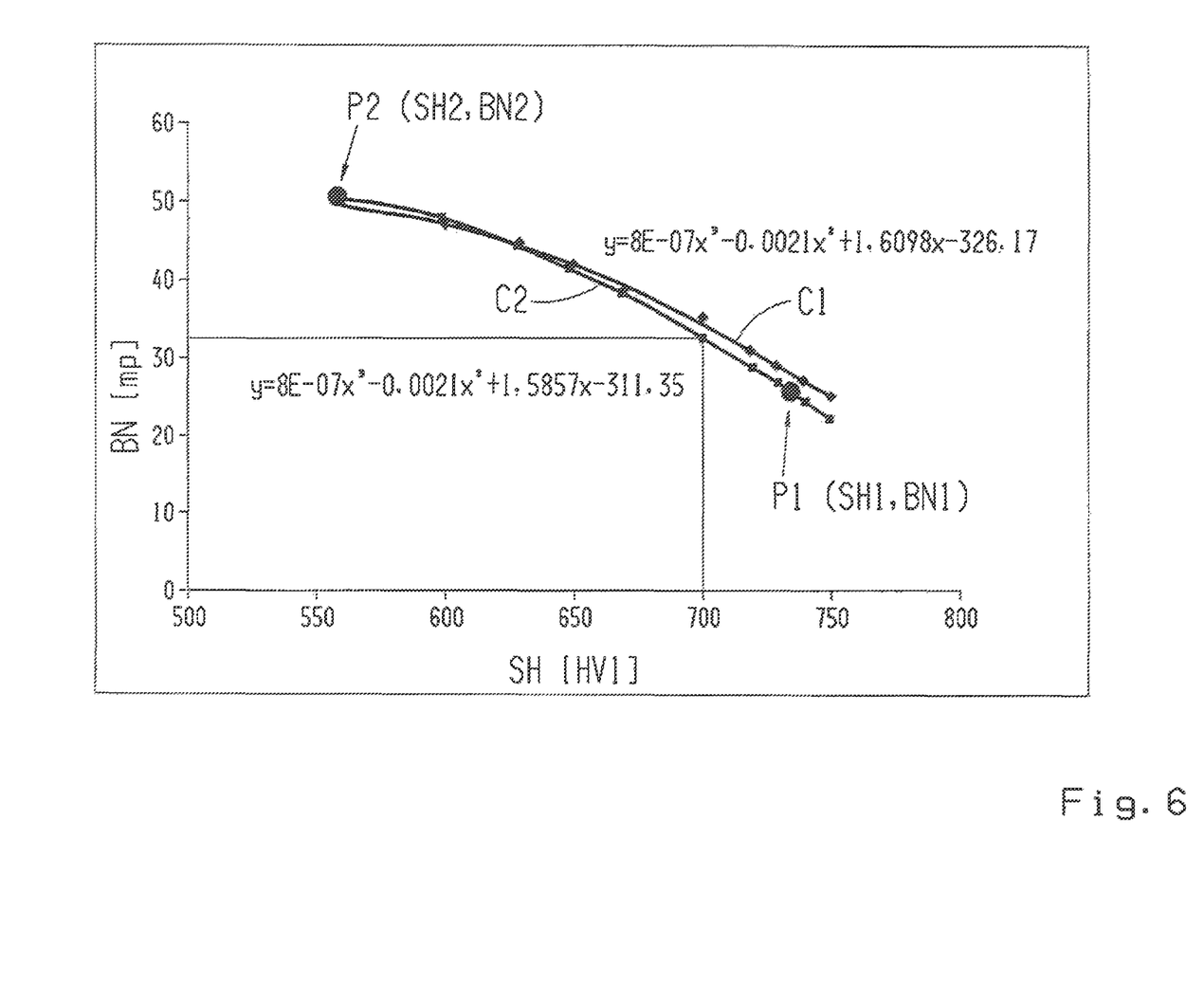
FIG. 6: A diagram illustrating the determination of a second calibration curve on the basis of the first calibration curve, in accordance with an embodiment of the invention.

During the calibration according to the invention, the BNA signal or a suitable mean value of the signals for the first reference component and for the second reference component are determined. Owing to the surface damage and the associated lower hardness, the BNA signal from the second reference component is of higher amplitude than the BNA signal from the first reference component. The corresponding correlations between the component surface hardness SH and the BNA signal BN are then used for adapting the first calibration curve C1. This is shown in FIG. 6. Analogously to FIG. 4, FIG. 6 shows the calibration curve C1. In addition, P1 represents the tuple of the surface hardness SH1 and the associated BNA signal BN1 for the first reference component. Likewise, the tuple P2 shows the correlation between the surface hardness SH2 and the Barkhausen noise signal BN2 for the second reference component. Finally, by means of a best-fit analysis the calibration curve is adapted to the values P1 and P2 in such manner that the calibration curve still represents the trend of the dependence of the Barkhausen noise on the surface hardness, but passes through or close to the points P1 and P2. A correspondingly adapted calibration curve is shown in FIG. 6 as the second curve C2. Furthermore, the corresponding polynomial equations for the calibration curve C1 (upper equation) and for the calibration curve C2 (lower equation) are given for the scenario represented.

As an example, an approach will be explained below to show how the calibration curve C1 can be appropriately adapted to the measurement tuples P1 and P2 of the reference components. This example is based on the assumption that the change of slope (second derivative) of the mathematical correlation between component surface hardness and BNA signal remains constant. In this case one begins with the following mathematical correlation in the form of a polynomial to describe the first calibration curve:

$$y' = f(x) = a_1 \cdot x^3 + a_2 \cdot x^2 + a_3 \cdot x + a_4 \qquad (2).$$

The first and second derivatives can then be expressed as follows:

$$y' = f'(x) = 3a_1 \cdot x^2 + 2a_2 \cdot x \qquad (3).$$

$$y'' = f''(x) = 6a_1 \cdot x + 2a_2 \qquad (4).$$

By subsequent integration a new approach function f_neu (x) is derived, whose unknowns D1 and D2 can be determined by using the measurement tuples P1 and P2 of the master components, so that the following mathematical description of the second calibration curve is obtained:

$$y = f\_neu(x) = a_1 \cdot x^3 + a_2 \cdot x^2 + D_1 \cdot x + D_2 \qquad (5).$$

In the scenario described here, a lower limit value for the component surface hardness is specified, which is predetermined for the corresponding component to be inspected. If the surface hardness falls below that value it is assumed that grinding burn has occurred. By means of the second calibration curve C2 that limit value for the hardness can now be linked to a corresponding upper limit of the Barkhausen noise signal, and if this upper limit is exceeded it an be assumed that the component has been damaged by grinding burn. In FIG. 6, for example, the lower limit for the component surface hardness SH is set at 700 HV1. Thus, by means of the second calibration curve C2, an upper limit for the Barkhausen noise signal of around 32 mp is obtained.

Besides a limit value for the minimum component surface hardness, which is linked to an upper limit value of the BNA signal, a limit value of the maximum component surface hardness is specified for the component to be inspected. This surface hardness should not be exceeded since otherwise the component becomes brittle. Excessively high surface hardness can occur for example due to heat treatment errors or due to grinding burn in the form of re-hardening. By analogy with the upper limit value of the BNA signal, in the calibration described here a lower limit value of the BNA signal is also determined by way of the calibration curve C2, which is based on the maximum value of the surface hardness. A correspondingly calibrated device detects any exceeding of the upper, or falling below the lower limit values of the BNA signal measured. In that event appropriate messages or an error signal are emitted, which indicate that the surface inspection of the component has given an abnormal result and the component must therefore be separated out.

In a particularly preferred embodiment of the method according to the invention, besides the above-described calibration a component-internal self-calibration of the measuring device is carried out whenever a component is measured, for the component just measured, which applies only for that component. This self-calibration is described in detail below and is also represented in FIG. 2. The background of the self-calibration method is that the BNA measurement signals depend not only on the surface hardness but on several other influencing factors as well. Examples are the tooth geometry (tooth width dimension), the setting up of the measurement program for guiding the sensor of the measuring device, and suchlike. Experience shows, however, that during mass production no component damaged by grinding burn is produced which does not have a good area somewhere in which the surface hardness is normal. The basic idea of component-internal self-calibration is based on that knowledge. In other words, the "good" area on a component to be measured, in which there is no grinding burn, is defined as a reference area. That area is classified as described for the above-mentioned first master component. On the basis of the BNA signals in the reference area, the aforesaid limit values for the BNA signal are appropriately shifted or adapted. In the embodiment described here the self-calibration is divided into the following steps:

1. Identification of reference areas with no grinding burn on the component just measured;
2. Plausibility testing of the measurement signals and identification of a rough characteristic;
3. Identification of a "good" area in accordance with the characteristic;
4. Shifting of the measurement signal of the first reference component;
5. Adaptation of the upper and lower limit for the BNA signal.

Figure 7A:
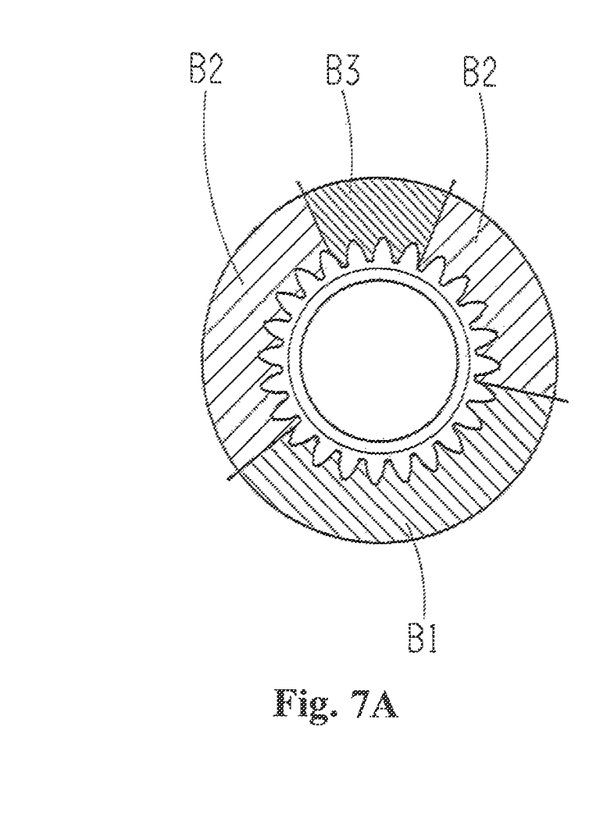
Figure 8:
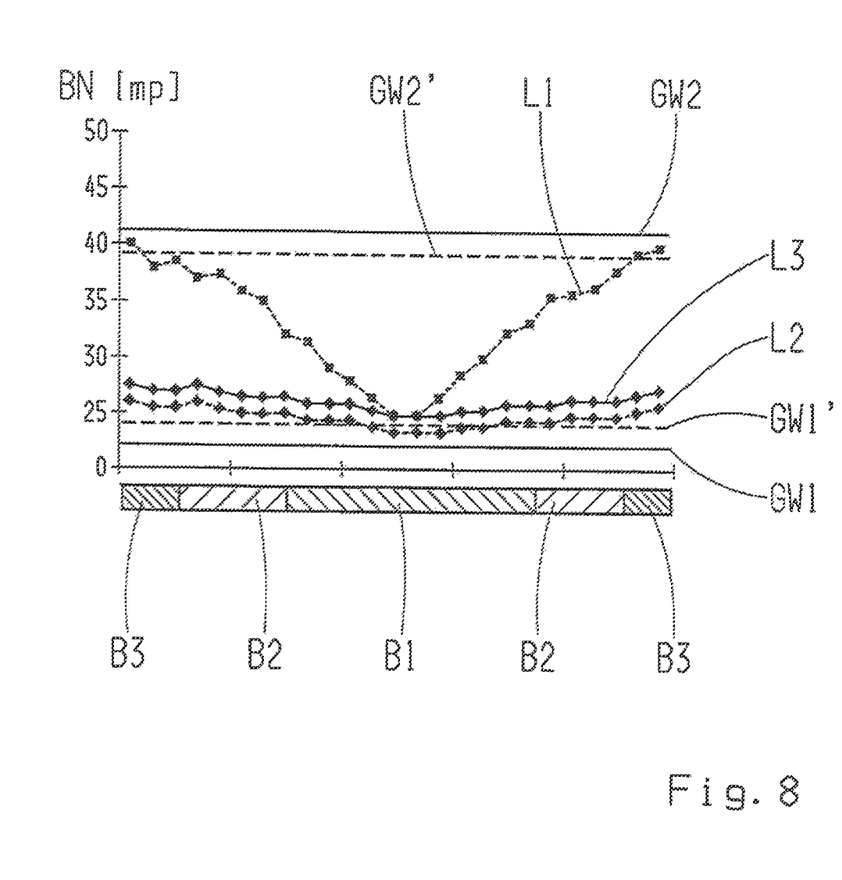
Figure 8A:
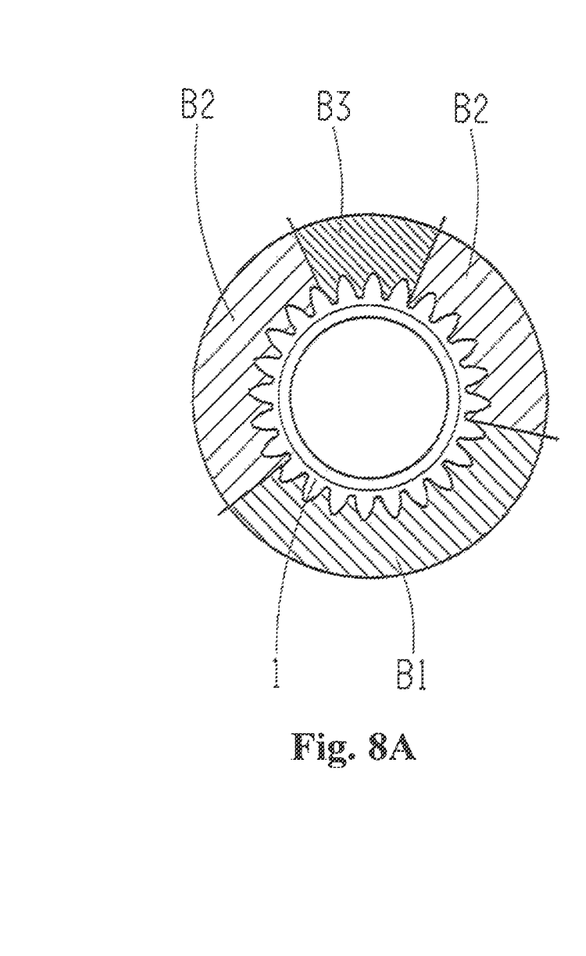

Below, the above steps will be explained as an example with reference to a gearwheel 1, which is shown sectioned in FIGS. 7A and 8A. In a first step the tooth flanks of the gearwheel are divided into flat squares. Each flat square has the minimum value of the signals measured in the flat square concerned. Then, a plausibility test is carried out. The purpose of this test is to check the BNA signals for comprehensibility and to discover and exclude possible measurement errors and re-hardening. The implementation of such a plausibility test lies within the scope of a trained person's common practice and makes use of general experience of testing for grinding burn. During this all the characteristics of grinding burn are taken into account. For example, the area with minimum signal values is always opposite the area with maximum signal values over the circumference of the gearwheel. If the difference between the minimum and maximum values is large, this corresponds to the characteristic of concentricity error. Another example is eccentric grinding during the production of the gearwheel. In accordance with this characteristic grinding burn only occurs on one side of the tooth flanks. Eccentric grinding is caused by a centering error of the grinding tool. During the plausibility test the existing characteristics are determined at the same time and the dominant characteristic is identified.

For a gearwheel, the dominant characteristic can be determined by whether large differences occur in the signals corresponding to the flat squares for different tooth flanks or for different circumferential regions. In this way it can be determined in a suitable manner by comparing the differences, whether the characteristic of concentricity error or that of eccentric grinding is dominant. Depending on the dominant characteristic, a "good" area on a tooth flank or a "good" circumferential section of the gearwheel is established. This "good" area shows the lowest BNA signal and the minimum value of the BNA signal in this reference area is then used for adapting the limit values, as described below. In the case of a serious concentricity error the good area will be in a section of the circumference of the component, whereas in contrast, in the case of an eccentricity error and when too much has been ground away from the tooth flank on the right, the good area is defined by the left flank.

Figure 7:
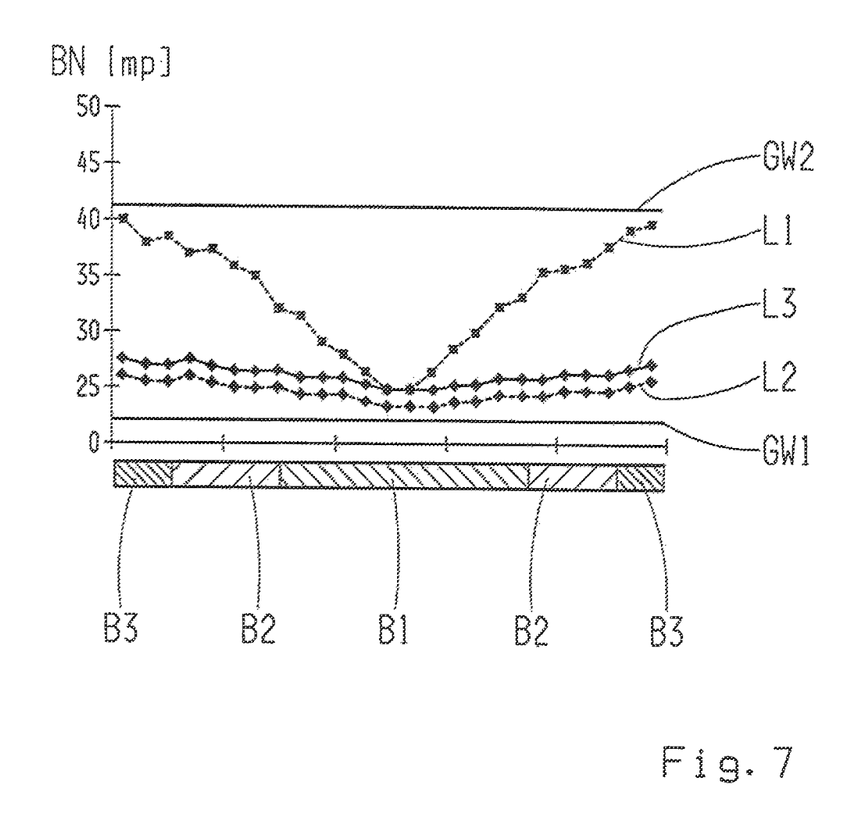
FIGS. 7, 7A, 8 and 8A: Schematic representations to make clear the modification of limit values for the Barkhausen noise signal, for components just measured, on the basis of an embodiment of the invention.

For the characteristic of a concentricity error FIG. 7 shows the corresponding definition of a good reference area with low BNA signals. Individual circumferential sections are specified by circular segments along the circumference of the gearwheel. In this case the reference area is identified as the area B1. Thus, that area has no surface damage. In contrast, the two adjacent areas B2 are circumferential areas with higher BNA measurement values, which are transition zones to the area B3 with the highest BNA signal and therefore the greatest risk from grinding burn.

FIG. 7, with regard to the cross-section of the gearwheel 1, a diagram is shown which pictures the Barkhausen noise signal BN (on the ordinate) along the various areas B1 to B3 (on the abscissa). The BNA signal for the gearwheel 1 takes the form of a curve L1. In addition, the curve L2 represents the Barkhausen noise signal measured along the circumference of the first reference component. Moreover, the lower limit value GW1 and the upper limit value GW2 are shown, which were determined with reference to the calibration curve C2 as described earlier. To adapt the limit values the area B1 without surface damage is now considered. In this case the curve L2 is displaced to the minimum value of the BNA signal of the curve L1 within this area, as indicated by the curve L3. In accordance with this displacement the lower limit value GW1 is adapted as can be seen in FIG. 8. FIG. 8 shows that the lower limit value GW1 has been displaced upward by the displacement path between curves L2 and L3. The displaced limit value is indexed GW1' and represented by a broken line. On the basis of the displacement a displacement of the upper limit value GW2 also takes place, in which the upper limit value GW2 moves downward to the modified limit value GW2', again indicated by a broken line.

The size and direction of the displacement of the limit value GW2 can be determined in advance by a suitable, set ratio. If necessary the said ratio can have the value 1. In that case the upper limit value is displaced through the same distance and in the same direction as the lower limit value. In a preferred variant, however, a suitable ratio is determined on the basis of one or more influencing parameters that have an influence on the limit values and hence on the BNA signals. One such influencing parameter, for example, is sensor wear. The calculation of a corresponding ratio for that influencing parameter, namely sensor wear, takes place in such manner that the corresponding calibration curves C2 as in FIG. 6 are determined for a measuring device with a severely worn sensor and for a measuring device with a less severely worn sensor, and from these the upper and lower limit values for the sensors with different wear severities are determined. Then, the quotient of the change of the upper limit value as a function of sensor wear and the change of the lower limit value as a function of sensor wear is formed. This ratio represents the factor by which the upper limit value is displaced as a function of the change of the lower limit value in accordance with FIG. 8. The ratio may possibly be negative, as is the case in FIG. 8, in which the displacement of the lower limit value upward leads to a displacement of the upper limit value downward.

If necessary other influencing factors too can be taken into account for estimating the ratio, for example differing tooth geometries, different contact conditions between the sensor and the surface, and the like. If the ratios for a number of influencing parameters are determined, that ratio is used for determining the displacement of the upper limit value which has the most dominant influence on the change of the limit values. That in turn can be determined by how marked the changes of the limit values were when the corresponding influencing parameters were being evaluated.

In a further variant of the method according to the invention, continuous calibration also takes place during the mass production of the components. For this, statistical methods are brought into play. Here, for the succession of identical components inspected an overall signal of the Barkhausen noise is determined. That signal is, for example, the mean value of all the Barkhausen noise signals that were determined for a surface of a component. In a run-up phase before the mass production begins, the overall signals from several identical components are determined. Starting from an initial statistical significance level, noticeable cases in the form of outriders are identified by a classical outrider recognition method such as the outrider test according to Grubbs. During this, for each component above the significance level, a corresponding tolerance range for the overall signal is determined. Components whose overall signal lies outside the tolerance rang are identified as outriders and initially classified as damaged. These components are cross-checked by some other test method such as hardness measurement or internal stress measurement. If after cross-checking, the component is found not to be damaged, the significance level is reduced and thus the tolerance range enlarged. Thus, after the recalculation of the tolerance range the component is no longer identified as damaged. If after cross-checking, the component concerned, which was recognized as an outrider, is still classified as damaged, the significance level remains unchanged and so too therefore does the tolerance range. If necessary such components can also be cross-checked whose signals, although within the tolerance range, are close to its limits (for example at 80% of the corresponding limit of the tolerance range). If those components are identified as damaged by the cross-check, the significance level is increased so that the tolerance range is made more narrow. The purpose of this process is to adapt the significance level such that both the non-recognition of damaged components and also the erroneous classification of components with no surface damage as damaged components are avoided as much as possible.

Figure 9:
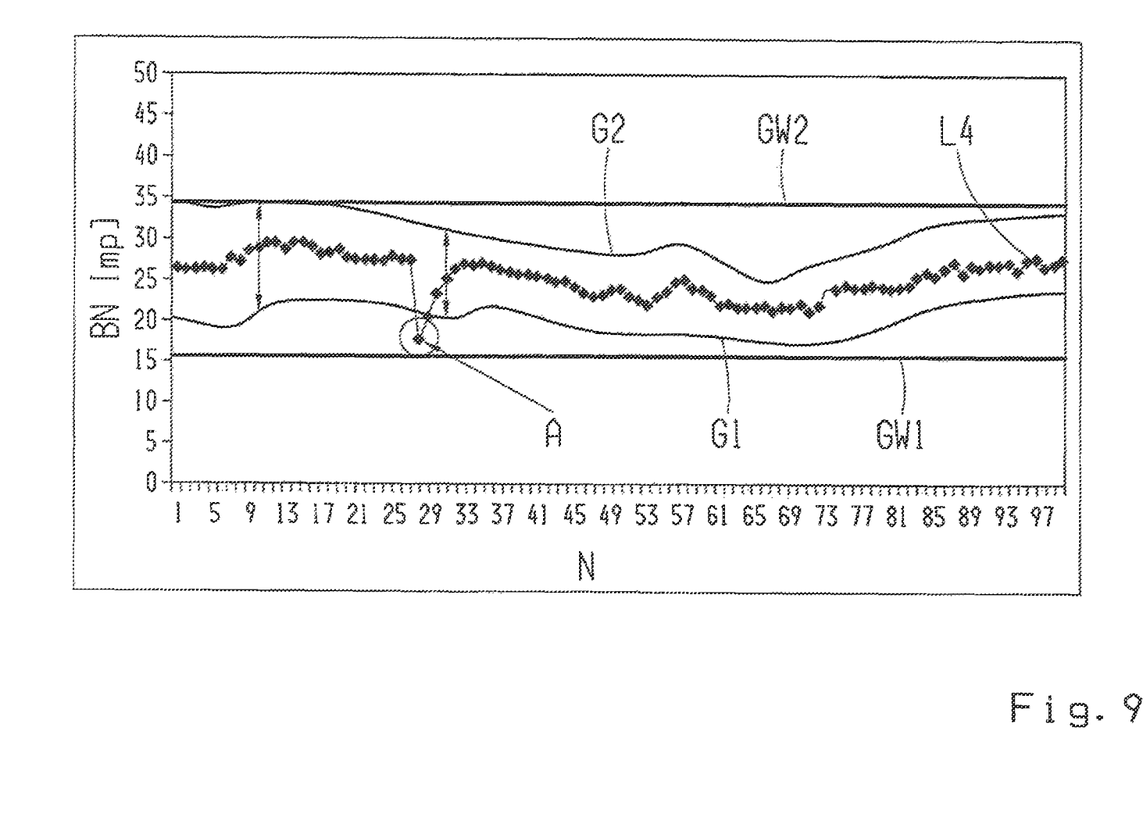
FIG. 9: A diagram illustrating the recognition of outriders during the statistical evaluation of Barkhausen noise signals, on the basis of an embodiment of the method according to the invention.

Once a suitable significance level has been determined during the run-up phase by the outrider recognition procedure, that significance level is then used during the serial measurement of the components as a further criterion for the determination of damaged components. This is illustrated in FIG. 9. In that diagram the corresponding numbers N of the components consecutively measured in a series are shown along the abscissa and the overall signals BN of the Barkhausen noise determined for those components are shown along the ordinate. The signals form the line L4. In addition, the lower and upper limits GW1 and GW2 are shown by analogy with FIGS. 7 and 8. For each new value of the overall signal a corresponding tolerance range is determined by way of the significance level determined during the run-up phase, which range is represented by a lower limit G1 and an upper limit G2. FIG. 9 also shows an outrider A, which represents a component having a signal outside the tolerance range. That component is then classified as damaged, whereupon for example a corresponding message can be emitted by the measuring device. If necessary, during the serial measurements an optimization of the tolerance range can take place. For this, an outrider can be randomly checked to see whether the component concerned is actually damaged. If not, the significance level and so too the tolerance range are adapted. the variant of a statistical evaluation of the Barkhausen noise signals just described is also illustrated in FIG. 2.

The embodiments of the method according to the invention described above have a series of advantages. In particular, compared with conventional calibration methods, the complexity of calibration to locate and adapt the limit values is substantially reduced. This is because during the calibration a rough calibration curve is used, which is independent of the component geometry and which has been produced during fundamental investigations carried out for each material in order to determine correlations between a phenomenon (grinding burn identified by Nital etching), physical component properties (component surface values) and a measured parameter (BNA signal) in relation to a particular material. That basis is then adapted specifically for the component, in that for the calibration two additional master-components are referred to, one with and one without surface damage, which form the correlation of the BNA signals in relation to the component type to be inspected. By means of an appropriate adaptation of the rough calibration to the BNA signals from the master-components, a suitable limit value for surface damage and in particular for grinding burn is determined. If necessary this calibration can be improved in two other ways, in particular the limit value can again be adapted by virtue of a component-internal self-calibration process.

Furthermore, by the statistical evaluation of mass-produced components a tolerance range can again be established, in order thereby to identify components with surface damage.

INDEXES

1 Component
101, 102 Teeth
M1, M2, M3, M4 Measurement lines
h, $b_M/2$ Height data
PS1, PS2, . . . PS9 Measurement points
SH Surface hardness
S Grinding burn degree
C1 First calibration curve
C2 Second calibration curve
BN Barkhausen noise signal
P1, P2 Measurement tuple
SH1 First surface hardness value
SH2 Second surface hardness value
BN1 First Barkhausen noise signal
BN2 Second Barkhausen noise signal
B1, B2, B3 Circumferential zones of a gearwheel
GW1, GW2, GW1'
GW2', G1, G2 Limit values
L1, L2, L3, L4 Curves
N Number of the component
A Outrider

The invention claimed is:

1. A method of calibrating a measuring device for surface inspection based on Barkhausen noise for a specific component geometry, the method comprising:
specifying a first calibration curve (C1) independent of the component geometry, which describes a relationship between surface hardness values (SH) and measured Barkhausen noise signals (BN);
determining, with the measuring device, a first Barkhausen noise signal (BN1) for a first reference component which corresponds to the specified component geometry and has a first surface hardness value (SH1);

determining, with the measuring device, a second Barkhausen noise signal (BN2) for a second reference component, which corresponds to the specified component geometry and has a second surface hardness value (SH2) that is lower than the first surface hardness value (SH1);

determining a second calibration curve (C2), in that the first calibration curve (C1) is adapted to the first Barkhausen noise signal (BN1) at the first surface hardness value (SH1) and to the second Barkhausen noise signal (BN2) at the second surface hardness value (SH2) such that, during operation of the measuring device, the measured Barkhausen noise signal (BN) of a component (1) having the specified component geometry is correlated, by means of the second calibration curve (C2), with a surface hardness value (SH).

2. The method according to claim 1, further comprising adapting the first calibration curve (C1) in such manner that the value of the second calibration curve (C2), at the first surface hardness value (SH1), corresponds to the first Barkhausen noise signal (BN1) and the value of the second calibration curve (C2), at the second surface hardness value (SH2), corresponds to the second Barkhausen noise signal (BN2).

3. The method according to claim 1, further comprising associating specified surface hardness values (SH) with respective limit values of the Barkhausen noise signal (BN) by way of the second calibration curve (C2).

4. The method according to claim 3, further comprising relating either the limit value or the limit values to grinding burn degrees (S) of a component (1) produced by grinding.

5. The method according to claim 1, further comprising defining the component with the specified component geometry as a gearwheel.

6. The method according to claim 1, further comprising experimentally determining the first calibration curve (C1).

7. The method according to claim 6, further comprising designing the experimental determination such that for a number of components, various degrees of experimentally determined surface damage are correlated with surface hardness values (SH) by measuring the surface hardness, and the various degrees of experimentally determined surface damage are correlated with Barkhausen noise signals (BN) by measuring the corresponding Barkhausen noises, and the first calibration curve (C1) is determined from the two correlations.

8. The method according to claim 1, further comprising producing the first reference component and the second reference component on a basis of a specified production process.

9. The method according to claim 8, further comprising using a different production process for the second reference component than a production process for the first reference component by at least using an additional heat treatment step of the component during the production process for the second reference component.

10. The method according to claim 1, further comprising specifying upper and lower hardness limit values for the surface hardness of a component (1) having the specified component geometry, and by way of the second calibration curve (C2), lower and upper limit values (GW1, GW2) for the Barkhausen noise signal (BN) are associated with the upper and the lower hardness limit values.

11. The method according to claim 10, further comprising determining a surface region (B1) with no surface damage for a component (1) with the specified component geometry that has just been inspected using the measuring device and, in a case when a minimum Barkhausen noise signal at the surface region (B1) with no surface damage is larger than the Barkhausen noise signal (BN) from the first reference component, increasing the lower limit value (GW1) by a difference between those two Barkhausen noise signals, and changing the upper limit value (GW2) as a function of the difference.

12. The method according to claim 1, further comprising determining, for each component (1), an overall signal of the Barkhausen noise, during the serial measurement of a large number of identical components (1), and by virtue of a statistical evaluation of overall signals from several identical components (1) during a run-up phase, prior to serial production, a significance level is determined on a basis of which, during serial measurements, a tolerance range is determined for each overall signal such that a result outside the tolerance range is detected.

13. The method according to claim 12, further comprising applying an outrider recognition process to the overall signals, during the statistical evaluation, and adapting the significance level depending on whether the outrider is a component (1) with or without surface damage.

14. The method according to claim 12, further comprising determining, during the serial measurements, by random sampling for overall signals outside the tolerance range, whether the corresponding component has surface damage, and if the component (1) has no surface damage, the tolerance range is enlarged.

15. A measuring device for surface inspection based on Barkhausen noises for a specified component geometry, the measuring device having a memory in which a first calibration curve (C1) that is independent of component geometry is stored, the first calibration curve describes a relationship between surface hardness values (SH) and measured Barkhausen noise signals (BN);

for a first reference component which corresponds to the specified component geometry and which has a first surface hardness value (SH1), a first Barkhausen noise signal (BN1) is determined by the measuring device during the calibration of the measuring device;

for a second reference component which corresponds to the specified component geometry and which has a second surface hardness value (SH2) that is lower than the first surface hardness value (SH1), a second Barkhausen noise signal (BN2) is determined by the measuring device during the calibration of the measuring device;

the measuring device having a computer unit which determines a second calibration curve (C2) during the calibration of the measuring device, in that the first calibration curve (C1) is adapted to the first Barkhausen noise signal (BN1) at the first surface hardness value (SH1) and to the second Barkhausen noise signal (BN2) at the second surface hardness value (SH2) such that, during operation of the measuring device, the measured Barkhausen noise signal (BN) of a component (1) with the specified component geometry is associated, by the second calibration curve (C2), with a surface hardness value (SH).

16. The measuring device according to claim 15, wherein the computer unit of the measuring device adapts the first calibration curve (C1) in such manner that the value of the second calibration curve (C2) at the first surface hardness value (SH1) corresponds to the first Barkhausen noise signal (BN1) and the value of the second calibration curve (C2) at the second surface hardness value (SH2) corresponds to the second Barkhausen noise signal (BN2).

17. A method of calibrating a measurement device which inspects component surfaces, having a specified geometry, based on Barkhausen noise signal measurements, the method comprising the steps of:
- defining at first calibration curve (C1) which is unaffected by the component geometry and which correlates surface hardness values (SH) and the Barkhausen noise signals of component surface;
- determining, with the measurement device, a first Barkhausen noise signal (BN1) for a first reference component, and the first reference component having the specified geometry and a first surface hardness value (SH1);
- determining, with the measurement device, a second Barkhausen noise signal (BN2) for a second reference component, and the second reference component having the specified geometry and a second surface hardness value (SH2) that is lower than the first surface hardness value (SH1);
- defining a second calibration curve (C2), in that the first calibration curve (C1) is adapted to the first Barkhausen noise signal (BN1) at the first surface hardness value (SH1) and to the second Barkhausen noise signal (BN2) at the second surface hardness value (SH2);
- measuring, with the measurement device, a Barkhausen noise signal (BN) of a subsequent component (1) having the specified geometry and being inspected, and the measured Barkhausen noise signal of the subsequent component is correlated to a surface hardness value (SH) of the subsequent component (1) by the second calibration curve (C2) so as to ascertain the surface hardness value (SH) of the subsequent components (1).

* * * * *